United States Patent
Ollivier

(10) Patent No.: US 9,327,112 B2
(45) Date of Patent: May 3, 2016

(54) LEFT VENTRICULAR INTRASEPTAL STIMULATION LEAD

(71) Applicant: SORIN CRM S.A.S., Clamart (FR)

(72) Inventor: Jean-François Ollivier, Villiers le Bacle (FR)

(73) Assignee: SORIN CRM S.A.S., Clamart Cedex (FR)

(*) Notice: Subject to any disclaimer, the term of this patent is extended or adjusted under 35 U.S.C. 154(b) by 83 days.

(21) Appl. No.: 14/052,145

(22) Filed: Oct. 11, 2013

(65) Prior Publication Data

US 2014/0107755 A1    Apr. 17, 2014

(30) Foreign Application Priority Data

Oct. 12, 2012  (FR) .................................. 12 59760

(51) Int. Cl.
*A61N 1/05*    (2006.01)
*A61N 1/375*   (2006.01)
*A61N 1/362*   (2006.01)

(52) U.S. Cl.
CPC ............... *A61N 1/059* (2013.01); *A61N 1/362* (2013.01); *A61N 1/375* (2013.01)

(58) Field of Classification Search
CPC ........ A61N 1/059; A61N 1/362; A61N 1/375
See application file for complete search history.

(56) References Cited

U.S. PATENT DOCUMENTS 7,104,988 B2 *  9/2006  Altman et al. .................. 606/41
7,340,288 B1    3/2008  Karicherla et al.
2001/0023367 A1  9/2001  King et al.
2008/0200769 A1 *  8/2008  Sharma et al. ................ 600/300
2008/0294229 A1 * 11/2008  Friedman et al. ............. 607/127

FOREIGN PATENT DOCUMENTS

| EP | 0 993 840 | 4/2000 |
| EP | 1 516 644 | 3/2005 |
| EP | 1 570 880 | 9/2005 |
| EP | 2 246 091 | 11/2010 |
| EP | 2 308 550 | 4/2011 |
| EP | 2 327 366 | 6/2011 |

(Continued)

OTHER PUBLICATIONS

Preliminary Search Report for French Patent Application No. 1259760, dated Feb. 19, 2013, 3 pages.

*Primary Examiner* — Rex R Holmes
(74) *Attorney, Agent, or Firm* — Foley & Lardner LLP

(57) ABSTRACT

A stimulation lead is disclosed. This lead comprises a lead body having a lumen housing an inner conductor, the conductor being axially and rotationally movable within the lumen, and coupled to a generator of an active implantable medical device. The lead also has a helical anchoring screw extending from a distal end configured to penetrate target tissue, and a stimulation needle electrically coupled to the conductor and comprising at its distal end an active free portion with at least one stimulation electrode for application of pacing pulses to the target tissue. The stimulation needle is axially movable between a retracted position inside the tubular body, and a deployed position with the active free portion of the needle emerging out of the tubular body, utilizing an actuating mechanism for moving the needle from its retracted position to its deployed position under the effect of rotary movement relative to the lead body.

20 Claims, 3 Drawing Sheets

(56) References Cited

FOREIGN PATENT DOCUMENTS

| | | |
|---|---|---|
| EP | 2 384 784 | 11/2011 |
| EP | 2 394 695 | 12/2011 |
| EP | 2 457 612 | 5/2012 |
| WO | WO-2012/073097 | 6/2012 |

* cited by examiner

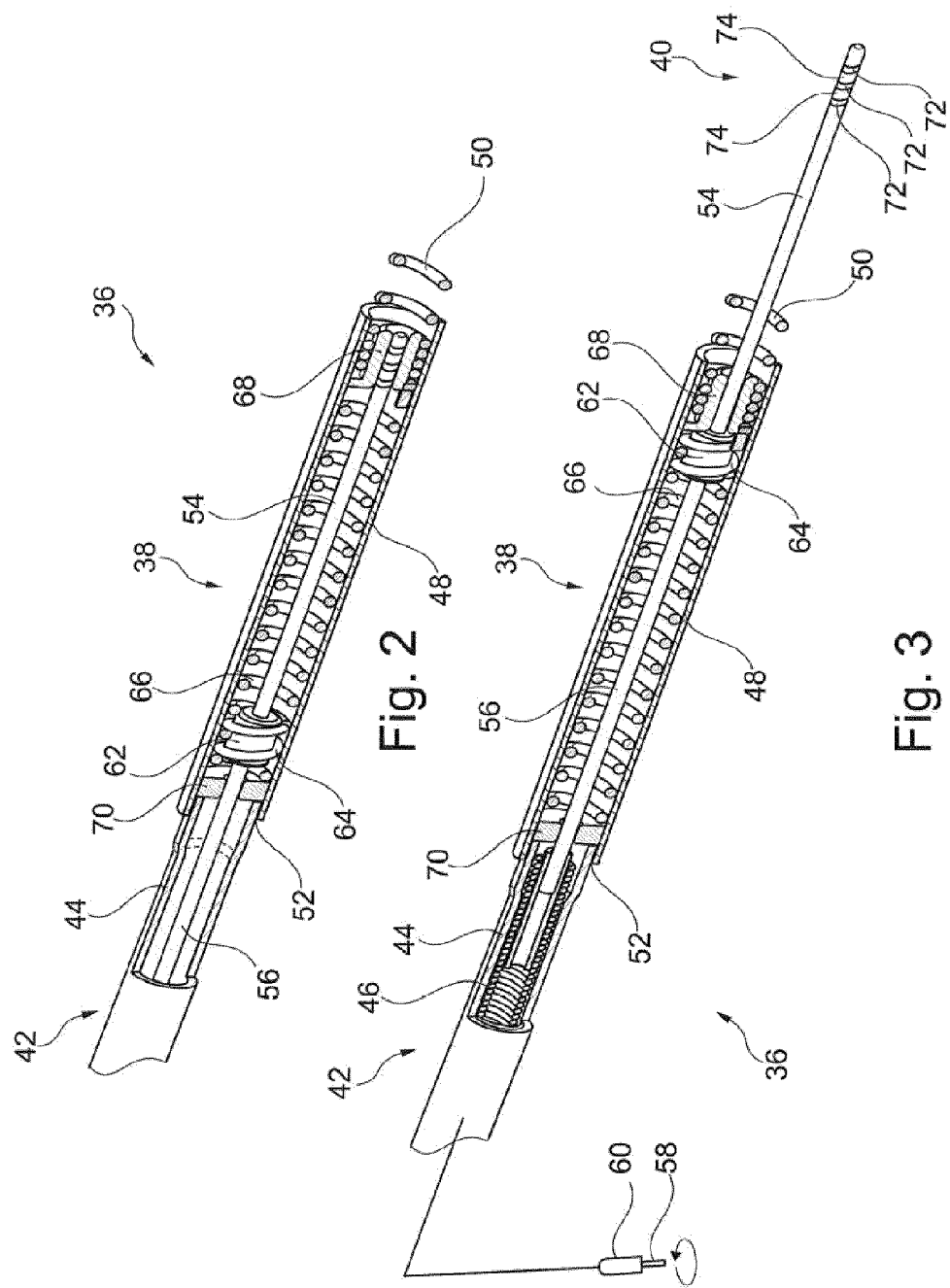

LEFT VENTRICULAR INTRASEPTAL STIMULATION LEAD

CROSS-REFERENCE TO RELATED APPLICATION

This application claims the benefit of and priority to French Patent Application No. 1259760, filed Oct. 12, 2012, which is incorporated herein by reference in its entirety.

BACKGROUND

The invention relates to intracardiac leads for pacing of the left ventricle. The invention is in the general context of "active implantable medical devices" as defined by Directive 90/385/EEC of 20 Jun. 1990 the Council of the European Communities, including implants to continuously monitor heart rhythm and deliver as necessary to the heart electrical stimulation, resynchronization or defibrillation pulses.

Intracardiac "stimulation" leads refers to leads for the delivery of low-energy pulses used for bradycardia or resynchronization therapies. The invention also applies to intracardiac leads for cardioversion/defibrillation intended to deliver a high energy electric shock to the heart to try to terminate a tachyarrhythmia. "Stimulation lead (or electrode)" or "stimulation/defibrillation lead" may refer to any kind of lead used for these or other similar purposes.

For stimulation of the right ventricle, the implantation of an endocardial lead through the right peripheral venous network is sufficient. However, to stimulate the left ventricle, the situation is more complex. The most commonly adopted solution is to introduce a lead, not into the cavity to stimulate, but in the coronary network, the lead being provided with an electrode applied against the wall facing the epicardium and oriented in direction of the left ventricle. These leads stimulate the heart muscle via one or more point electrodes, the position of which is a function of the predefined trajectory of the cannulated vein. A lead of this type is for example the Situs LV model marketed by Sorin CRM (Clamart, France) and described in EP 0993840 A1 (ELA Medical). The introduction of such a lead is made via the coronary sinus, because of its opening in the right atrium. The lead is then pushed and oriented along the network of coronary veins to the selected site. Once the target vein is reached, the surgeon looks for a satisfying stimulation site, and with a good electrical contact of the stimulation electrode against the tissue of the epicardium. This contact is maintained despite various variations or stresses over time. This implantation technique is not always feasible, especially when the shape of the coronary sinus is too rough, or in case of thrombosis. Indeed, the precise positioning of the electrode(s) to stimulate the left ventricle through the myocardial wall is a critical parameter, and it is not always possible to reach effective stimulation sites.

Another more difficult and much more invasive technique involves an implantation of epicardial electrodes on the outer wall of the myocardium, in one or more suitable sites facing the cavity of the left ventricle. A variant of this technique, described in EP 2308550 A1 (Sorin CRM), involves the implantation of the electrode, formed by the conductive helical screw of a screw lead, via a bent catheter inserted into the pericardial sac. However, these techniques are relatively invasive and also generally irreversible, since it is very difficult to change the implantation site initially chosen, and to explant, if necessary, the lead at a later stage.

Another approach, to which the invention pertains, is to stimulate the left ventricle by applying pacing pulses to the wall of the interventricular septum (the wall separating the left ventricle and the right ventricle) by means of a lead inserted into the right ventricle using a traditional approach. This technique involves the drilling of the atrial or ventricular septum, then the introduction of a lead through this septum until it comes into contact with a point on the wall of the left ventricle. The stimulation pulses are then applied directly to the left endocardial site thus selected. For an example of a controlled transeptal puncture technique, one may refer to EP 1516644 A1 (ELA Medical), which describes a guiding accessory having one end closed by an anchoring screw to the right wall of the septum, and in which a piercing stylet is inserted for initiating a puncture of the septum. After withdrawal of the piercing stylet, a guiding stylet is inserted in the accessory, to form an axial guide in which the pacing lead, provided with its electrodes, is then introduced in the left cavity after removal of the accessory.

Another technique for making a transeptal puncture, described by EP 2327366 A1 (Sorin CRM) is to anchor a screw to the septum wall, and then to apply to this screw radiofrequency energy to progressively sink into the septum wall until it passes through the latter. The puncture can also be performed by a guide-wire supplied with the RF energy, which is pushed to cross from one side to the other the septum.

These techniques have several drawbacks, mainly due to the fact that they require making a puncture in the septal wall of a diameter sufficient to insert a guide-catheter for establishing a communication between the right and left cavities through the wall, to then insert the left endocardial stimulation lead. Because the element opening into the left ventricle element is a hollow catheter, this results in significant risk of air embolism. To avoid this risk, it is imperative to take many precautions when handling haemostatic valves, meeting purge equipment procedures, etc. However, given the highly invasive nature of the procedure, uncertainties remain about the behavior in the long-term blood circulation, which involves anticoagulation to prevent thromboembolism post-operatively. Finally, subsequent extraction of the lead is practically impossible, because of the excessive risks that would be incurred at the crossing of the septum.

In any case, these techniques are very difficult to implement and require great skill of the practitioner, who, before crossing the septum, must always ensure perfect positioning of the piercing needle on the wall, crossing the septum having to be undertaken only if there is not any doubt left about the position of the needle, to avoid accidental dissection of the walls by a sudden movement of the needle piercing the septum—hence the development of specific drilling kits, such as those described in EP 1516644 A1 and EP 2327366 A1 above.

Yet another technique designed to reduce these risks is described by EP 2457612 A1 and EP 2384784 (Sorin CRM). The basic idea is to remove the guide catheter associated to a lead crossing the septum, and replace this set by a conventional lead screwed onto the wall of the right ventricle at the septum, extending the lead by a transeptal microcable, partially isolated and pushed into the left ventricle to come into contact against a target located in this ventricle, for example against the free wall of the latter (that is to say the wall located opposite to the septal wall).

Due to the extreme thinness of the puncture (the size of which being that of the microcable diameter), this technique greatly reduces the risks associated with previous techniques. However, insofar as the microcable is freely deployed in the left ventricle, it is difficult to control the delivery of pacing pulses at specific sites, and to ensure adequate and continuous contact between the electrodes of this free part and the wall of the left ventricle because of the physical instability of the microcable on the free wall resulting from the very high flexibility of the microcable. In addition, the transmission of the puncture push via the microcable can be difficult: indeed, the need for mechanical endurance requires great flexibility for the microcable, flexibility that is not compatible with the necessary requirement of "pushability" (ability to transmit axial pushing forces applied from the proximal end) during the puncture step.

SUMMARY

In some embodiments of the invention, to overcome these various drawbacks and limitations, the following step is provided: extending a screw lead anchored on the right wall of the interventricular septum, with a very fine telescopic needle, so as to be minimally invasive. The needle is extended so as to puncture the septum thickness, but without or almost without emerging of the left side wall. The screw is in principle passive (it has only a mechanical role) but the tip of the needle is active, with one or more electrodes that can precisely reach the left branch of the His bundle: this branch is indeed a rapid conduction line, and effective and without delay for the stimulation of the left ventricle even in case, for example, of a local left block. As will be seen, the lead is provided with means for precise adjustment of puncture depth, to achieve the desired target area according to a perfectly gradual and controlled method, in addition involving only the usual conventional operative procedures for the practitioner.

A technique such as that taught by EP 2457612 A1 and EP 2384784 above, which is intended to implant a microcable pushed through the septum into the left ventricle to come into contact against a target in the ventricle (e.g. against the free wall of the latter, located opposite the septal wall) is however not applicable in the present case, of an intraseptal—and not a transeptal—stimulation needle.

Indeed, insofar as the stimulation must occur at the septum, the position of the tip of the needle may be finely adjusted. The active part bearing the stimulation electrode(s), may be finely adjusted to lie within the thickness of the septum after implantation. This is not possible with a technique of simply pushing a microcable in a sheath, a technique that is inadequate to ensure millimeter precision required for intraseptal implantation. WO 2012/073097 A2 and U.S. 2001/0023367 A1 describe mechanisms of insertion of needles in different, not relating to cardiac pacing, contexts.

In an exemplary embodiment, a lead body with a flexible hollow sheath is provided. The lead body includes a central lumen housing an inner conductor axially and rotationally mobile within the lumen. On a proximal end, an electrical connector is connected to the generator of an active implantable medical device, said connector having at least one central pin connected to the inner conductor. On the distal end, a lead head with a tubular body integral with the sheath is provided. The lead head includes a distally extended anchoring helical screw. The lead head extends into the cavity of the right ventricle and the anchoring screw penetrates into the right ventricular septal wall under the effect of a screwing movement of the sheath of the lead body from the proximal end of the lead.

The lead further comprises a stimulation needle, electrically connected to the inner conductor and comprising at its distal end an active free part with at least one stimulation electrode for application of the stimulation pulses. This needle is an axially movable telescopic needle between a retracted position inside the tubular body, and a fully or partially deployed position with the free active portion of the needle emerging out of the tubular body.

To enable intraseptal stimulation by the needle, wherein said pulses are applied to the septum in a region near the left wall of the region thereof, the lead further comprises an actuating mechanism for production of a controlled movement of the needle from its retracted position to its partially or fully extended position under the effect of a movement of relative rotation of the connector pin relative to the lead body, this movement being transmitted to the pin from the proximal end of the lead. The actuating mechanism comprises a guiding core secured to the needle in rotation and in translation and movable in translation and in rotation inside the tubular body, and means of coupling of the core to the tubular body, for conversion of a relative rotation movement of the core to the tubular body in an axial translation movement of the core inside the tubular body.

According to various embodiments:

The means of coupling may be screw-nut means having an internal helical thread of the tubular body member cooperating with a conjugate element that engages with the thread of the tubular body, in particular a helical thread carried by an outer surface of the core;

The inner conductor may be a coiled conductor arranged in a peripheral region of the hollow sheath;

The amplitude of the axial translation movement of the core inside the tubular body may be between 10 and 15 mm;

The length of the protruding part of the needle in the extended position may be between 0 and 15 mm, and has a diameter of 1.5 French (0.5 mm);

The outer surface of the needle may be electrically insulated, except for at least one exposed area, located in the active free portion, forming said at least one stimulation electrode;

The free active portion may comprise at least one exposed area extending over no more than 6 mm from the free distal end of the needle;

The lead may comprise a plurality of exposed distinct zones successively extending along the active free part and separated by not exposed insulating spacers zones;

The total area of the exposed zone(s) of the active part may be no more than 6 mm$^2$;

At its proximal portion, the needle may be extended by a rod to which it is integral and which is welded to the inner conductor;

The anchoring screw and/or the tubular body may be electrically inactive.

BRIEF DESCRIPTION OF THE FIGURES

FIGS. 2 and 3 are sectional views of the lead head, respectively, in the retracted position and the extended position of the stimulation needle.

DETAILED DESCRIPTION

Figure 1:
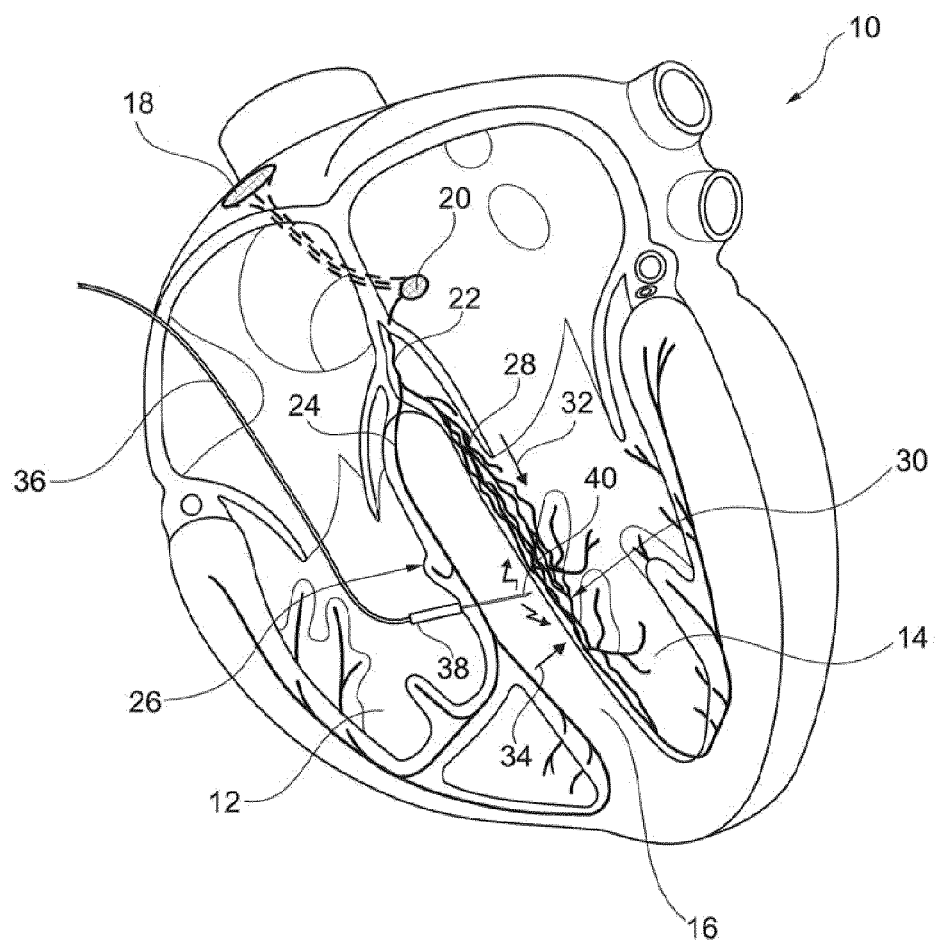
FIG. 1 is a schematic sectional view of the myocardium, showing its different cavities and the main electrical conduction paths.

FIG. 1 is a schematic sectional view of the myocardium 10 with the right ventricle 12 and the left ventricle 14 separated by the interventricular septum 16. It has a typical thickness of about 10 to 15 mm and constitutes a significant portion of the cardiac mass.

The depolarization waves that originate in the sinoatrial node 18 are transmitted to the atrioventricular node 20 and the His bundle 22, which is divided into two branches extending along the septum 16, with a straight branch 24 in the region the right septal wall 26 and a left branch 28 in the region of the left septal wall 30.

In particular, the left branch 28 is a line of fast longitudinal electrical conduction (arrow 32), with a speed of about 4 m/s. However, the conventional techniques implementing retractable screw leads can stimulate the right wall 26, so that to stimulate the left ventricle 14, the waves of depolarization must cross the septum 16 (arrow 34), but with a speed of cross conduction relatively low, on the order of 0.4 m/s. This introduces a delay of about 30 ms between the application of the pulse on the right portion 26 and the excitement of the left branch 28 leading to contraction of the left ventricle 14.

Moving the point of stimulation of the right wall of the septum (conventional technique) to the left wall of the septum, close to the left branch 28 of the His bundle (technique of the invention), can significantly contribute to reduce the time between the application of the pulse and the actual contraction of the left ventricle, and/or mitigate the effects of a local left block. According to the invention, a lead 36, implanted in a conventional manner in the right cavities, with a lead head 38 anchored against the right wall 26 of the septum 16, is used for this purpose. The lead head 38 is extended by a telescopic needle whose distal end 40 carries the stimulation electrodes. A gradual and controlled puncture of the septum 16 allows placement of the end 40 of the needle in the vicinity of the left wall 30 without passing through the septum 16, or only barely opening of this wall, so as to directly stimulate the left branch 28 of the His bundle exactly in the area of rapid conduction, thereby providing a direct and immediate stimulation of the left ventricle 14.

FIGS. 2 and 3 more particularly illustrate, respectively in the retracted position and the extended position of the telescopic needle, the structure of the lead head 38 located at the distal end of the lead 36, and intended to abut against the right septal wall. The lead body 42 includes an insulated flexible hollow sheath 44, for example of a material such as polyurethane which has very good sliding properties when the sheath is inserted into a delivery catheter, and "torquability", that is to say, the ability to transmit to the distal end a torque from the proximal end of the lead. The inner lumen of the hollow sheath 44 houses one or more internal conductors, such as in the example shown, a coiled conductor 46 disposed in a peripheral region of the hollow sheath so as to leave a free central space, notably for the insertion of a guiding and/or stiffening stylet within the sheath. If the sheath has a number of internal conductors, the configuration can be advantageously "coradial", wherein two (or more) conductors are side-by-side coiled insulated conductors in a peripheral region of the inner lumen of the hollow sheath 44 and forming a coil of single radius on one unique thickness.

The sheath 44 of the lead is extended to its distal end by a tubular body 48 having an outer diameter of about 7 French (2.33 mm). This tubular body 48 carries at its distal end a helical anchoring screw 50, which can project over an axial length of about 2 mm. Said helical screw is secured to the tubular body 48 which, at its opposite proximal end is secured at a location 52 to the hollow sheath 44. Thus, any rotational movement of the lead body under the effect of a particular torque applied from the proximal end of the lead by the practitioner will be fully transmitted to the helical screw 50 via the tubular body 48, the three elements being integral with each other.

A lead screw implanted similar to what has just been described is generally used as detection/stimulation lead after anchoring of the screw at the site of endocardial stimulation.

In the case of the invention this is not the case: the function of the screw is here to serve as means for supporting and guiding a stimulation needle punctured in the wall of the septum. For the implementation of the invention, the screw 50 and the tubular body 48 are not (or not necessarily) electrically active elements.

The tubular body 48 houses, in the retracted position (FIG. 2), a telescopic stimulation needle 54 which is axially movable in translation relative to the tubular body 48, between the retracted position of FIG. 2 and an extended position illustrated in FIG. 3. Proximally, the telescopic needle 54 is extended by an axial rod 56, for manoeuvre, welded proximal side to the distal end of the inner conductor 46, so that any axial or rotation movement of this inner conductor 46 is fully transmitted to the needle 54. In addition, the needle 54 is not only mechanically but also electrically connected to the inner conductor 46.

The proximal end of the inner conductor 46 is connected to a pin 58 of a connector 60 for coupling to the housing of a pulse generator. This is, for example, a standard IS-1 connector or the like, with a pin 58 movable in rotation relative to the connector body 60, so as to allow pin-driven manipulation, in which the practitioner holds in one hand the body of the connector 60 (integral with the sheath 44 of the lead body 42) and applies rotation with the other hand, directly or via a tool, the pin 58 of the connector. The pin 58 is integral with the axial conductor 46, itself free in rotation within the hollow sheath 44, the movement of the pin directly transmitted to the spindle 56 and to the telescopic needle 54.

The telescopic needle 54 is a solid needle, so as not to present any hollow element in the left ventricle in case the needle crosses through the septum, therefore not creating any risk of air embolism.

The guiding and the deployment of the telescopic needle 54 are controlled by a movable member 62 within the tubular body 48 and forming a guiding and driving core. This core 62, integral with the rod 56, is coupled to the tubular body, for example by an external thread 64 integral with the core 62, cooperating with an internal thread 66 integral with the tubular body 44. Thus, a movement of relative axial rotation of the rod 56 relative to the tubular body 48 (resulting from a corresponding movement of relative rotation of the pin 58 relative to the connector 60 proximal side) results in an axial translation of the driving core 62, and thus of the telescopic needle 54 relative to the tubular body 48.

The magnitude of this axial displacement is typically of the order of 10 to 15 mm and has a value significantly greater than that of a conventional deployment mechanism of the screw of a retractable screw lead.

Flexible bearings 68 and 70 are respectively provided distal and proximal side of the tubular body 48 for guiding of the needle and for sealing of the interior volume of the tubular body and of the lumen of the hollow sheath 44.

In the retracted state (FIG. 2), the needle 54 is entirely housed inside the tubular body 48, from which only the helical anchoring screw 50 protrudes, which is fixed relative to the tubular body 48.

In the fully deployed state (FIG. 3), the telescopic needle 54 emerges from the tubular body on a length of about 15 mm. The needle may be deployed in a controlled manner between any of these extreme positions, thus on the length between 0 and 15 mm, in a method adjustable by the practitioner.

The telescopic needle 54 may be made of a conductor material and may have a diameter of 1 French (0.33 mm). The material can be a stainless alloy such as MP35N, or can be constituted by a composite structure, for example with a core in MP35N and a peripheral biocompatible and radiopaque, such as platinum or a platinum alloy, coating.

Alternatively, the intraseptal stimulation needle 54 may be made from a microcable having a diameter of about 1.5 F (0.5 mm), which allows it to benefit from the relative flexibility of the latter compared with a monofilament configuration of the same diameter, with thus better fatigue resistance. Such a microcable may include a core comprising a plurality of composite wires stranded together, e.g. with a central strand surrounded by six peripheral strands. Each composite strand is itself made up of a wire the core of which is of platinum-iridium (for radiopacity) surrounded by a plurality of also composite wires providing the required mechanical and electrical properties, for example with a core of silver (for electrical conductivity) wrapped by nitinol (for the properties of resistance to mechanical stress). These different wires are commercially available, for example from the Fort Wayne Metals Company Inc., Fort Wayne, USA, and are used in the medical field in particular to manufacture defibrillation conductors.

The telescopic stimulation needle 54 is coated with an electrically insulating material, such as parylene. To form the active free part 40, the insulating coating of the needle is locally removed in order to make one or more denuded regions 72 separated by insulating regions 74. Advantageously, the active free part 40 having these denuded areas 72 extends over a length of about 6 mm, the surface of the denuded regions being at most 6 mm² to limit the stimulating surface.

Having a plurality of electrodes 72 on a relatively important length (6 mm) offers the possibility to compensate for variations in the thickness of the septum which contracts during a cardiac cycle, and thus to maintain a stimulating surface vis-à-vis the tissue.

From an electrical point of view, the anchoring screw 50 and the tubular body 48 are in principle inactive, and coated with an insulating material such as Parylene on their entire surface. In specific configurations, however, it is possible to make electrically the anchoring screw 50 and/or all or part of the tubular body 48 active, for example to allow simultaneous stimulation at the anchoring screw (right wall of the septum) and of the active free part 40 of the telescopic needle (left wall of the septum).

The method to implant the lead just described above will now be made with reference to FIGS. 4a to 4e.

The lead can be inserted into a conventional catheter 76, for the pre-positioning of the lead head against the wall of the ventricular septum. This catheter has a typical outside diameter of 9 French (3 mm). The use of a catheter allows protection of the anchoring screw 50 (which is not a telescopic screw) during the passage through the vessels and the crossing of the tricuspid valve. Examples of suitable catheters allowing access to the right wall of the interventricular septum are described for example in EP 2135638 A1 (pre-shaped catheter, self-adjustable in the direction of the septum wall) and in FR 2932688 A1 (bimaterial catheter whose end is conformable at will), both on behalf of Sorin CRM S.A.S., previously known as ELA Medical.

The first phase is to identify the anchoring site, by handling the lead-catheter assembly for introduction into the superior vena cava, the right atrium and the right ventricle 12 until it abuts against the right wall 26 of the interventricular septum 16.

Figure 4A:
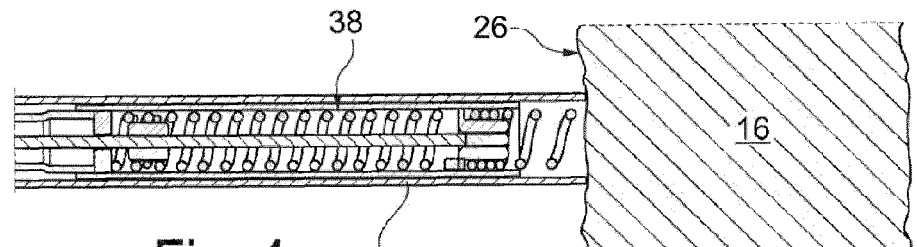
FIGS. 4a-4e illustrate the various stages of implantation in the wall of the interventricular septum of the lead of the invention.

FIG. 4a illustrates the configuration reached when the catheter 76 is brought into abutment against the right wall of the septum 16, with the lead head 38 placed inside the catheter 76 to the vicinity of this wall 26.

Figure 4B:
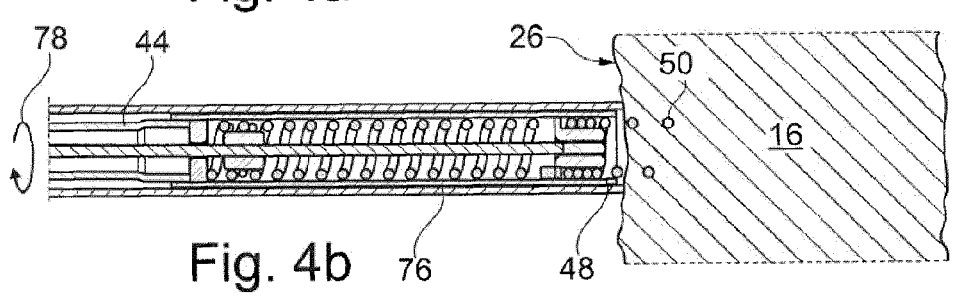
Figure 4C:
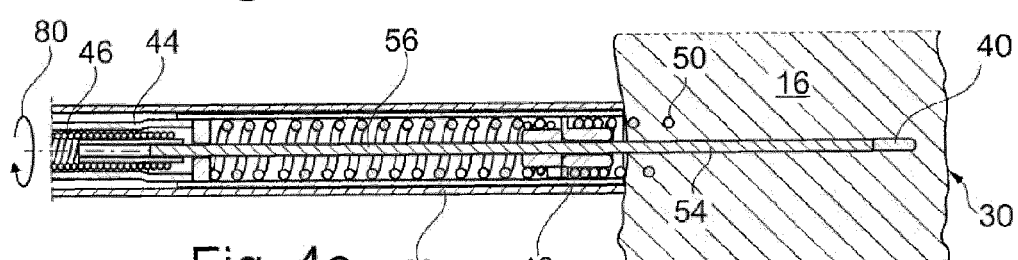

The next step, illustrated in FIG. 4b, is to give to the sheath 44 of the lead body a rotation movement (arrow 78) from the proximal end of the lead body. This rotation causes the screw 50 to penetrate into the tissue of the septum 16 on a relatively small depth (of the order of 2 mm), thereby anchoring the tubular body 48, to which the screw is integral with, against the right wall 26 of the septum. Full screwing is tactilely detected by the practitioner by the opposed resistance to the rotation.

The reached site is confirmed by radiographic examination according to different impacts; if the position is not satisfactory, the practitioner can unscrew the lead head and move it under control to another point and then test the new site.

Once the tubular body 48 is thus anchored to the wall of the septum, the practitioner imparts a rotation to pin 58 of connector 60. This rotation transmitted by the inner conductor 46 (arrow 80, FIG. 4c) is applied to the operating rod 56 which, consequently, causes the gradual penetration of the telescopic stimulation needle 54 into the thickness of the septum 16, since the lead body, and thus the sheath 44 and the tubular body 48, are held stationary during this deployment.

This handling is performed under fluoroscopy in order to visualize the position of the active portion 40 relative to the walls of the septum (which can optionally be visualized by injection of contrast medium through the catheter 76). The practitioner can also make at this stage a mapping or electrical testing to verify the effectiveness of the chosen site, in order to determine the optimum positioning of the active portion 40 of the needle, that is to say, the degree of deployment thereof.

If the site originally chosen is not satisfactory, it is possible to operate one or more repositionings. Indeed, the anchoring of the screw 50 in a relatively small thickness (about 2 mm for a typical thickness of the interventricular septum of 10 to 15 mm) and the very small diameter of the puncture (due to the very small diameter of the needle 55, in the order of 0.3 mm) are used to remove the lead without causing irreversible damage to the septum—and this contrasts to a conventional transeptal approach, less tolerant to error due to the size of the remaining puncture (corresponding to a catheter of a diameter, typically about 9 French or 2.3 mm).

The more or less important deployment of the telescopic needle 54 allows taking into account not only the septum thickness variations according to the region of implantation, but also to reflect the fact that the lead can be positioned in a position more or less perpendicular to the wall of the septum (which, in cross section, has a convex shape).

Once the final site and the degree of deployment of the telescopic needle are selected, the practitioner removes the catheter 76, resulting in the final configuration of the lead head.

Figure 4D:
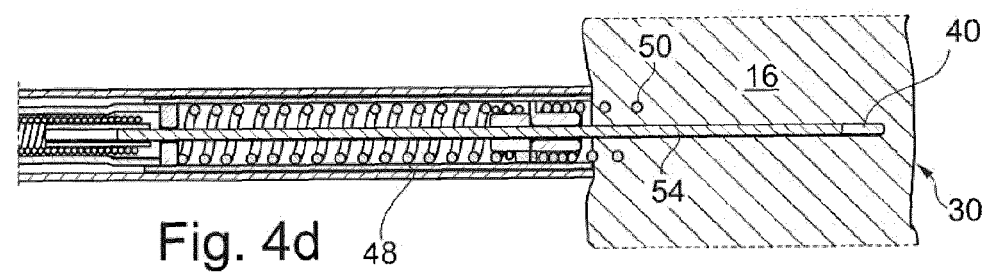

In the configuration shown in FIG. 4d, the distal end 54 of the needle (with the active part 40) does not emerge from the left wall 30 of the septum.

Figure 4E:
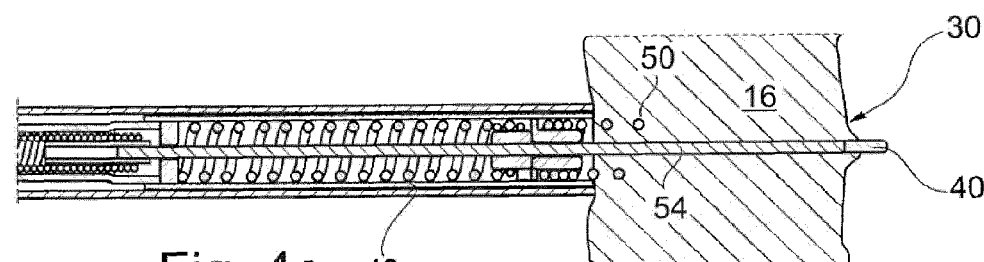

However, as shown in FIG. 4e, in certain instances the needle can be caused to pass completely through the septum to position the free end 40 of the needle 54 so that it slightly emerges in the cavity of the left ventricle. This avoids the effect of shelling of the end of the needle to the target tissue, which can lead to their destruction and therefore to a loss of capture during pacing.

The invention claimed is:

1. A pacing lead, comprising:
   a lead body comprising a hollow sheath housing an inner conductor, wherein the inner conductor is axially and rotationally movable within the hollow sheath, wherein the inner conductor terminates at a distal end of the hollow sheath, and the lead body having at a proximal end an electrical connector for coupling the inner conductor to a generator of an active implantable medical device;

the lead body further comprising a tubular body having a proximal end and a distal end, wherein the proximal end of the tubular body receives the distal end of the hollow sheath;

a helical anchoring screw extending from a distal end of the tubular body, integral with the tubular body, wherein the helical anchoring screw is configured to penetrate a wall of a target tissue under the effect of a rotary movement of the lead body from the proximal end of the lead;

a stimulation needle electrically coupled at its proximal end to the distal end of the inner conductor and comprising at its distal end an active free portion providing at least one stimulation electrode for application of pacing pulses to the target tissue;

wherein the stimulation needle is axially movable between a retracted position inside the tubular body, and a deployed position with the active free portion of the needle emerging out of the tubular body; and an actuating mechanism providing a controlled movement of the needle from its retracted position to its deployed position under the effect of rotary movement relative to the tubular body;

the actuating mechanism comprising a core coupled to a proximal portion of the stimulation needle, and secured in rotation and in translation within the tubular body by at least one coupling member, and movable in rotation and in translation with respect to the tubular body.

2. The lead of claim 1, wherein said coupling member comprises an external thread which cooperates with a counterpart internal helical thread of the tubular body.

3. The lead of claim 1, wherein the rotary movement relative to the lead body is transmitted from a proximal end of the inner conductor coupled to the stimulation needle.

4. The lead of claim 1, wherein the inner conductor is a coiled conductor arranged in a peripheral region of the hollow sheath.

5. The lead of claim 1, wherein the core inside the tubular body has an axial translation range of between 10 and 15 mm.

6. The lead of claim 1, wherein the needle in the deployed position extends past the proximal end of the tubular body by a length between 0 and 15 mm.

7. The lead of claim 1, wherein the needle is at most 1.5 French (0.5 mm) in diameter.

8. The lead of claim 1, wherein the needle includes an outer surface that is electrically insulated except for at least one exposed area, situated in the active free portion, forming at least one stimulation electrode.

9. The lead of claim 8, comprising a plurality of distinct exposed areas extending in succession along the active free portion and separated by insulated intermediate zones.

10. The lead of claim 1, wherein the electrical connector comprises at least one central pin connected to the inner conductor.

11. The lead of claim 1, wherein the proximal end of the needle is extended by a rod to which it is integral, and wherein the rod is welded to the inner conductor.

12. The lead of claim 1, wherein the helical anchoring screw is electrically inactive.

13. The lead of claim 1, wherein the tubular body is electrically inactive.

14. The lead of claim 1, wherein the lead is an intracardiac left ventricle pacing lead comprising the helical anchoring screw for penetrating an interventricular septum having a right wall and a left wall, wherein the lead penetrates the right wall, and at least one stimulation electrode for application of pacing pulses to the interventricular septum in a region adjacent to the left wall thereof.

15. A method for stimulating an interventricular septum of a heart, the interventricular septum having a right wall and a left wall and the heart having a left ventricle, the method comprising:

implanting a stimulation lead in the interventricular septum of the heart by:
inserting an assembly comprising a catheter and a stimulation lead into the heart until the assembly abuts against the right wall of the interventricular septum;
wherein the stimulation lead comprises a lead body having a proximal end, a distal end, a hollow sheath housing an inner conductor, the conductor being coupled to a generator of an active implantable medical device and wherein the inner conductor terminates at a distal end of the hollow sheath, and a tubular body having a proximal end and a distal end, wherein the proximal end of the tubular body receives the distal end of the hollow sheath, and the lead body having at a proximal end an electrical connector for coupling the inner conductor to a generator of an active implantable medical device;
the stimulation lead further comprising a helical anchoring screw extending from the distal end of the lead body, integral with the lead body;
imparting rotational movement on the proximal end of the lead body which rotates the helical anchoring screw to penetrate the interventricular septum and secure the lead body thereto;
wherein the stimulation lead further comprises a stimulation needle electrically and mechanically coupled at its proximal end to a distal end of the inner conductor and comprising at its distal end an active free portion with at least one stimulation electrode;
moving the stimulation needle from a retracted position inside the lead body to a deployed position by rotating the stimulation needle relative to the lead body, wherein in the deployed position the stimulation needle extends at least partially into the interventricular septum into a region adjacent to the left wall of the interventricular septum;
removing the catheter from the body; and
providing pacing pulses from the active implantable medical device through the at least one stimulation electrode to stimulate the region adjacent to the left wall of the interventricular septum.

16. The method of claim 15, wherein the stimulation needle extends through the interventricular septum such that a portion of the distal end of the needle extends into the left ventricle.

17. The method of claim 15, wherein the lead body comprises at its proximal end an electrical connector for coupling the inner conductor to the generator of the implantable medical device, and wherein the electrical connector comprises at least one central pin connected to the inner conductor.

18. The method of claim 17, wherein the stimulation needle further comprises an actuating mechanism comprising a core coupled to a proximal portion of the stimulation needle, and secured in rotation and in translation within the lead body by at least one coupling member, and wherein moving the stimulation needle from a retracted position inside the lead body to a deployed position comprises imparting rotational movement on a proximal end of the inner conductor which causes the core to move in rotation and translation relative to the lead body.

19. The method of claim 18, wherein moving the stimulation needle from a retracted position inside the lead body to a deployed position comprises imparting rotational movement on a central pin connected to the inner conductor.

20. A lead, comprising:
   a lead body comprising a hollow sheath housing an inner conductor, wherein the inner conductor is axially and rotationally movable within the hollow sheath, and wherein the inner conductor terminates at a distal end of the hollow sheath, and the lead body having a proximal end;
   the lead body further comprising a tubular body having a proximal end, wherein the proximal end of the tubular body receives the distal end of the hollow sheath;
   a lead anchor extending from a distal end of the lead body;
   a stimulation needle electrically coupled at its proximal end to the distal end of the inner conductor and comprising at its distal end an active free portion providing at least one stimulation electrode for application of pacing pulses to a target tissue;
   wherein the stimulation needle is axially movable between a retracted position inside the tubular body, and a deployed position with the active free portion of the needle emerging out of the tubular body; and
   an actuating mechanism providing a controlled movement of the needle from its retracted position to its deployed position under the effect of rotary movement relative to the lead body.

* * * * *